(12) United States Patent
Sabahi et al.

(10) Patent No.: US 11,926,796 B2
(45) Date of Patent: *Mar. 12, 2024

(54) FCC CATALYST WITH MORE THAN ONE SILICA, ITS PREPARATION AND USE

(71) Applicant: Albemarle Corporation, Charlotte, NC (US)

(72) Inventors: Amir Sabahi, Missouri City, TX (US); Andrew J Loebl, Charlotte, NC (US); Sandra Gavalda, Manvel, TX (US); Julie Francis, Webster, TX (US); Eswaramoorthi Iyyamperumal, Houston, TX (US)

(73) Assignee: Ketjen Limited Liability Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/865,555

(22) Filed: Jul. 15, 2022

(65) Prior Publication Data
US 2022/0348829 A1 Nov. 3, 2022

Related U.S. Application Data

(62) Division of application No. 16/322,779, filed as application No. PCT/US2017/045580 on Aug. 4, 2017, now Pat. No. 11,427,764.

(Continued)

(51) Int. Cl.
| | |
|---|---|
| *B01J 29/06* | (2006.01) |
| *B01J 29/00* | (2006.01) |
| *B01J 29/08* | (2006.01) |
| *B01J 29/40* | (2006.01) |
| *B01J 29/70* | (2006.01) |
| *B01J 29/80* | (2006.01) |
| *B01J 29/83* | (2006.01) |
| *B01J 29/85* | (2006.01) |
| *B01J 35/00* | (2006.01) |
| *B01J 37/00* | (2006.01) |
| *B01J 37/03* | (2006.01) |

(Continued)

(52) U.S. Cl.
CPC ............. *C10G 11/05* (2013.01); *B01J 29/005* (2013.01); *B01J 29/06* (2013.01); *B01J 29/061* (2013.01); *B01J 29/084* (2013.01); *B01J 29/085* (2013.01); *B01J 29/088* (2013.01); *B01J 29/40* (2013.01); *B01J 29/70* (2013.01); *B01J 29/7007* (2013.01); *B01J 29/7038* (2013.01); *B01J 29/7057* (2013.01); *B01J 29/80* (2013.01); *B01J 29/83* (2013.01); *B01J 29/85* (2013.01); *B01J 35/0013* (2013.01); *B01J 37/0009* (2013.01); *B01J 37/0045* (2013.01); *B01J 37/036* (2013.01); *B01J 37/038* (2013.01); *B01J 37/10* (2013.01); *B01J 37/28* (2013.01); *B01J 37/30* (2013.01); *C10G 11/18* (2013.01); *B01J 2029/062* (2013.01); *B01J 2029/081* (2013.01); *B01J 2229/36* (2013.01); *B01J 2229/42* (2013.01); *C07C 2527/14* (2013.01); *C07C 2527/16* (2013.01); *C07C 2527/167* (2013.01); *C07C 2527/18* (2013.01); *C07C 2527/182* (2013.01); *C07C 2529/06* (2013.01); *C07C 2529/08* (2013.01); *C07C 2529/40* (2013.01); *C07C 2529/70* (2013.01); *C07C 2529/83* (2013.01); *C07C 2529/85* (2013.01)

(58) Field of Classification Search
CPC ..... C10G 11/05; C10G 11/18; C07C 2527/14; C07C 2527/16; C07C 2527/167; C07C 2527/18; C07C 2527/182; C07C 2529/08; C07C 2529/40; C07C 2529/70; C07C 2529/83; C07C 2529/85; B01J 35/0013; B01J 37/0009; B01J 37/0045; B01J 37/036; B01J 37/038; B01J 37/10; B01J 37/28; B01J 37/30; B01J 2229/36; B01J 2229/42; B01J 2229/186; B01J 2029/062; B01J 2029/081; B01J 29/005; B01J 29/06; B01J 29/061; B01J 29/084; B01J 29/085; B01J 29/088; B01J 29/40; B01J 29/70; B01J 29/7007; B01J 29/7038; B01J 29/7057; B01J 29/80; B01J 29/83; B01J 29/85

USPC ........ 502/60, 63, 64, 65, 67, 68, 69, 71, 73, 502/77, 79, 84, 208
See application file for complete search history.

(56) References Cited

U.S. PATENT DOCUMENTS

| | | |
|---|---|---|
| 4,086,187 A | 4/1978 | Lim et al. |
| 4,206,085 A | 6/1980 | Lim |

(Continued)

FOREIGN PATENT DOCUMENTS

| | | |
|---|---|---|
| CN | 1247885 A | 3/2000 |
| EP | 2027917 | 7/2007 |

(Continued)

OTHER PUBLICATIONS

International Search Report and Written Opinion re Application No. PCT/US2017/045580 dated Nov. 9, 2017.

*Primary Examiner* — Elizabeth D Wood

(57) ABSTRACT

Process for the preparation of a catalyst and a catalyst comprising the use of more than one silica source is provided herein. Thus, in one embodiment, the invention provides a particulate FCC catalyst comprising about 5 to about 60 wt % one or more zeolites, about 15 to about 35 wt % quasicrystalline boehmite (QCB), about 0 to about 35 wt % microcrystalline boehmite (MCB), greater than about 0 to about 15 wt % silica from sodium stabilized basic colloidal silica, greater than about 0 to about 30 wt % silica from acidic colloidal silica or polysilicic acid, and the balance clay and the process for making the same. This process (Continued)

results in attrition resistant catalysts with a good accessibility.

3 Claims, No Drawings

Related U.S. Application Data

(60) Provisional application No. 62/370,809, filed on Aug. 4, 2016.

(51) Int. Cl.
*B01J 37/10* (2006.01)
*B01J 37/28* (2006.01)
*B01J 37/30* (2006.01)
*C10G 11/05* (2006.01)
*C10G 11/18* (2006.01)

(56) References Cited

U.S. PATENT DOCUMENTS

| | | |
|---|---|---|
| 4,458,023 A | 7/1984 | Welsh et al. |
| 6,858,556 B2 | 2/2005 | Kuvettu et al. |
| 7,517,827 B2 | 4/2009 | Ravichandran et al. |
| 9,381,502 B2 | 7/2016 | Stamires et al. |
| 9,534,177 B2 | 1/2017 | Babitz |

FOREIGN PATENT DOCUMENTS

| | | |
|---|---|---|
| EP | 1863588 B1 | 11/2017 |
| GB | 1315553 | 5/1973 |
| JP | H10146529 A | 6/1998 |
| WO | 1996009890 | 4/1996 |
| WO | 2002098563 | 12/2002 |
| WO | 2006067154 A1 | 6/2006 |
| WO | 2007006047 | 1/2007 |

FCC CATALYST WITH MORE THAN ONE SILICA, ITS PREPARATION AND USE

REFERENCE TO RELATED APPLICATIONS

This application is a divisional of U.S. application Ser. No. 16/322,779, filed on Feb. 1, 2019, which is the National Stage of International Patent Application No. PCT/US2017/045580 filed on Aug. 4, 2017, which in turn claims the benefit of U.S. Provisional Patent Application No. 62/370,809, filed on Aug. 4, 2016, the disclosures of which are incorporated herein by reference.

FIELD OF THE INVENTION

The present invention pertains to a catalyst composition and its use in a process for the cracking or conversion of a feed comprised of hydrocarbons, such as, for example, those obtained from the processing of crude petroleum, with better physical properties and performance.

BACKGROUND

A common challenge in the design and production of heterogeneous catalysts is to find a good compromise between the effectiveness and/or accessibility of the active sites and the effectiveness of the immobilising matrix in giving the catalyst particles sufficient physical strength, i.e. attrition resistance.

The preparation of attrition resistant catalysts is disclosed in several prior art documents. U.S. Pat. No. 4,086,187 discloses a process for the preparation of an attrition resistant catalyst by spray-drying an aqueous slurry prepared by mixing (i) a faujasite zeolite with a sodium content of less than 5 wt % with (ii) kaolin, (iii) peptised pseudoboehmite, and (iv) ammonium polysilicate. The attrition resistant catalysts according to U.S. Pat. No. 4,206,085 are prepared by spray-drying a slurry prepared by mixing two types of acidified pseudoboehmite, zeolite, alumina, clay, and either ammonium polysilicate or silica sol.

GB 1 315 553 discloses the preparation of an attrition resistant hydrocarbon conversion catalyst comprising a zeolite, a clay, and an alumina binder. The catalyst is prepared by first dry mixing the zeolite and the clay, followed by adding an alumina sol. The resulting mixture is then mixed to a plastic consistency, which requires about 20 minutes of mixing time. In order to form shaped particles, the plastic consistency is either pelletised or extruded, or it is mixed with water and subsequently spray-dried. The alumina sol disclosed in this British patent specification comprises aluminium hydroxide and aluminium trichloride in a molar ratio of 4.5 to 7.0 (also called aluminium chlorohydrol).

U.S. Pat. No. 4,458,023 relates to a similar preparation procedure, which is followed by calcination of the spray-dried particles. During calcination, the aluminium chlorohydrol component is converted into an alumina binder. WO 96/09890 discloses a process for the preparation of attrition resistant fluid catalytic cracking catalysts. This process involves the mixing of an aluminium sulphate/silica sol, a clay slurry, a zeolite slurry, and an alumina slurry, followed by spray-drying. During this process, an acid- or alkaline-stable surfactant is added to the silica sol, the clay slurry, the zeolite slurry, the alumina slurry and/or the spray-drying slurry. CN 1247885 also relates to the preparation of a spray-dried cracking catalyst. This preparation uses a slurry comprising an aluminous sol, pseudoboehmite, a molecular sieve, clay, and an inorganic acid. In this process the aluminous sol is added to the slurry before the clay and the inorganic acid are added, and the molecular sieve slurry is added after the inorganic acid has been added. According to one embodiment, pseudoboehmite and aluminium sol are first mixed, followed by addition of the inorganic acid. After acidification, the molecular sieve is added, followed by kaolin.

WO 02/098563 discloses a process for the preparation of an FCC catalyst having both a high attrition resistance and a high accessibility. The catalyst is prepared by slurrying zeolite, clay, and boehmite, feeding the slurry to a shaping apparatus, and shaping the mixture to form particles, characterised in that just before the shaping step the mixture is destabilised. This destabilisation is achieved by, e.g., temperature increase, pH increase, pH decrease, or addition of gel-inducing agents such as salts, phosphates, sulphates, and (partially) gelled silica. Before destabilisation, any peptisable compounds present in the slurry must have been well peptised.

WO 06/067154 describes an FCC catalyst, its preparation and its use. It discloses a process for the preparation of an FCC catalyst having both a high attrition resistance and a high accessibility. The catalyst is prepared by slurrying a clay, zeolite, a sodium-free silica source, quasi-crystalline boehmite, and micro-crystalline boehmite, provided that the slurry does not comprise peptised quasi-crystalline boehmite, b) adding a monovalent acid to the slurry, c) adjusting the pH of the slurry to a value above 3, and d) shaping the slurry to form particles.

BRIEF DESCRIPTION OF THE INVENTION

The present invention relates to an FCC catalyst meant to be employed in the process for cracking, a hydrocarbon feed over a particular catalyst composition to produce conversion product hydrocarbon compounds of lower molecular weight than feed hydrocarbons, e.g., product comprising a high gasoline fraction. A unique feature of the invention is the use of more than one silica source.

Thus, in one embodiment, provided is a particulate FCC catalyst comprising about 5 to about 60 wt % one or more zeolites, about 15 to about 35 wt % quasicrystalline boehmite (QCB), about 0 to about 35 wt % microcrystalline boehmite (MCB), greater than about 0 to about 15 wt % silica from sodium stabilized basic colloidal silica, greater than about 0 to about 30 wt % silica from acidic colloidal silica or polysilicic acid, and the balance clay.

In another embodiment, provided is a process for manufacturing an FCC catalyst, wherein the process comprises:
(a) Adding, clay, boehmite and sodium stabilized basic colloidal silica to form a slurry;
(b) Digesting the slurry with a monoprotic acid to a pH of less than 4;
(c) Adding one or more zeolites to the slurry;
(d) Adding polysilicic acid made separately and added inline;
(e) Mixing the slurry and then destabilizing the slurry by raising the pH to above 4.0
(f) Shaping and collecting the resulting FCC Catalyst;
(g) Optionally followed by a calcination step and post washing step to remove excess sodium as necessary.

In another embodiment, provided is a process for manufacturing an FCC catalyst, wherein the process comprises:
(a) Adding, clay, boehmite, sodium stabilized basic colloidal silica to form a slurry;
(b) Digesting the slurry with a monoprotic acid to a pH of less than 4;

(c) Adding one or more zeolites to the slurry;
(d) Adding the acidic colloidal silica at any time during or after steps (a)-(c) but before step (e);
(e) Mixing the slurry and then destabilizing the slurry by raising the pH to above 4.0;
(f) Shaping and collecting the resulting FCC Catalyst.

The resulting catalyst shows improved benefits over that known in the art. For example, the improved catalyst exhibits improved attrition and higher ABD and accessibility. Further, the improved catalyst results in higher zeolite and catalyst stability after deactivation.

In a still further embodiment, provided is a process for cracking a petroleum fraction feedstock said process comprising the steps of:
a) providing an FCC catalyst composition comprising about 5 to about 60 wt % one or more zeolites, about 15 to about 35 wt % quasicrystalline boehmite, about 0 to about 35 wt % microcrystalline boehmite, greater than about 0 to about 15 wt % silica from sodium stabilized basic colloidal silica, greater than about 0 to about 30 wt % silica from acidic colloidal silica or polysilicic acid, and the balance clay;
b) contacting the FCC catalyst with said petroleum fraction feedstock at a temperature in the range of from 400 to 650° C., with a dwell time in the range of from 0.5 to 12 seconds.

These and still other embodiments, advantages and features of the present invention shall become further apparent from the following detailed description, including the appended claims.

DETAILED DESCRIPTION OF THE INVENTION

Unless otherwise indicated, weight percent (_wt %) as used herein is the dry base weight percent of the specified form of the substance, based upon the total dry base weight of the product for which the specified substance or form of substance is a constituent or component. It should further be understood that, when describing steps or components or elements as being preferred in some manner herein, they are preferred as of the initial date of this disclosure, and that such preference(s) could of course vary depending upon a given circumstance or future development in the art.

General Procedure

The first step of the process of manufacturing the improved catalyst is to mix clay sources, with sodium stabilized basic colloidal silica, and one or more alumina (boehmite) sources. As will be discussed below, one can optionally add a second silica source of acidic colloidal silica to this slurry or at a later step. The clay, zeolite, QCB, MCB, sodium stabilized basic colloidal silica, and optional other components can be slurried by adding them to water as dry solids. Alternatively, slurries containing the individual materials are mixed to form the slurry according to step a). It is also possible to add some of the materials as slurries, and others as dry solids. Optionally, other components may be added, such as aluminium chlorohydrol, aluminium nitrate, $Al_2O_3$, $Al(OH)_3$, anionic clays (e.g. hydrotalcite), smectites, sepiolite, barium titanate, calcium titanate, calcium-silicates, magnesium-silicates, magnesium titanate, mixed metal oxides, layered hydroxy salts, additional zeolites, magnesium oxide, bases or salts, and/or metal additives such as compounds containing an alkaline earth metal (for instance Mg, Ca, and Ba), a Group IIIA transition metal, a Group IVA transition metal (e.g. Ti, Zr), a Group VA transition metal (e.g. V, Nb), a Group VIA transition metal (e.g. Cr, Mo, W), a Group VIIA transition metal (e.g. Mn), a Group VIIIA transition metal (e.g. Fe, Co, Ni, Ru, Rh, Pd, Pt), a Group IB transition metal (e.g. Cu), a Group IIB transition metal (e.g. Zn), a lanthanide (e.g. La, Ce), or mixtures thereof. Any order of addition of these compounds may be used. It is also possible to combine these compounds all at the same time.

The term "boehmite" is used in the industry to describe alumina hydrates which exhibit X-ray diffraction (XRD) patterns close to that of aluminium oxide-hydroxide [AlO(OH)]. Further, the term boehmite is generally used to describe a wide range of alumina hydrates which contain different amounts of water of hydration, have different surface areas, pore volumes, specific densities, and exhibit different thermal characteristics upon thermal treatment. Yet their XRD patterns, although they exhibit the characteristic boehmite [AlO(OH)] peaks, usually vary in their widths and can also shift in their location. The sharpness of the XRD peaks and their location has been used to indicate the degree of crystallinity, crystal size, and amount of imperfections.

Broadly, there are two categories of boehmite aluminas: quasi-crystalline boehmites (QCBs) and micro-crystalline boehmites (MCBs). In the state of the art, quasi-crystalline boehmites are also referred to as pseudo-boehmites and gelatinous boehmites. Usually, these QCBs have higher surface areas, larger pores and pore volumes, and lower specific densities than MCBs. They disperse easily in water or acids, have smaller crystal sizes than MCBs, and contain a larger number of water molecules of hydration. The extent of hydration of QCB can have a wide range of values, for example from about 1.4 up to about 2 moles of water per mole of Al, intercalated usually orderly or otherwise between the octahedral layers. Some typical commercially available QCBs are Pural®, Catapal®, and Versal® products.

Microcrystalline boehmites are distinguished from the QCBs by their high degree of crystallinity, relatively large crystal size, very low surface areas, and high densities. Contrary to QCBs, MCBs show XRD patterns with higher peak intensities and very narrow half-widths. This is due to their relatively small number of intercalated water molecules, large crystal sizes, the higher degree of crystallization of the bulk material, and the smaller amount of crystal imperfections. Typically, the number of water molecules intercalated can vary in the range from about 1 up to about 1.4 per mole of Al. A typical commercially available MCB is Condea's P-200®.

MCBs and QCBs are characterised by powder X-ray reflections. The ICDD contains entries for boehmite and confirms that reflections corresponding to the (020), (021), and (041) planes would be present. For copper radiation, such reflections would appear at 14, 28, and 38 degrees 2-theta. The exact position of the reflections depends on the extent of crystallinity and the amount of water intercalated: as the amount of intercalated water increases, the (020) reflection moves to lower values, corresponding to greater d-spacings. Nevertheless, lines close to the above positions would be indicative of the presence of one or more types of boehmite phases. For the purpose of this specification we define quasi-crystalline boehmites as having a (020) reflection with a full width at half height (FWHH) of 1.5° or greater than 1.5° 2θ. Boehmites having a (020) reflection with a FWHH of smaller than 1.5° 2θ are considered micro-crystalline boehmites. The slurry preferably comprises about 1 to about 50 wt %, more preferably about 15 to about 35 wt %, of non-peptised QCB based on the final catalyst. The slurry also comprises about 1 to about 50 wt %, more preferably about 0 to about 35 wt % of MCB based on the final catalyst.

Also the clay is preferred to have a low sodium content, or to be sodium-free. Suitable clays include kaolin, bentonite, saponite, sepiolite, attapulgite, laponite, hectorite, English clay, anionic clays such as hydrotalcite, and heat- or chemically treated clays such as meta-kaolin. The slurry preferably comprises about 5 to about 70 wt %, more preferably about 10 to about 60 wt %, and most preferably about 10 to about 50 wt % of clay.

In a next step, a monovalent acid is added to the suspension, causing digestion. Both organic and inorganic monovalent acids can be used, or a mixture thereof. Examples of suitable monovalent acids are formic acid, acetic acid, propionic acid, nitric acid, and hydrochloric acid. The acid is added to the slurry in an amount sufficient to obtain a pH lower than 7, more preferably between 1 and 4.

In the next step, one or more zeolites are added. The zeolites used in the process according to the present invention preferably has a low sodium content (less than 1.5 wt % $Na_2O$), or is sodium-free. Suitable zeolites to be present in the slurry of step a) include zeolites such as Y-zeolites—including HY, USY, dealuminated Y, RE-Y, and RE-USY—zeolite beta, ZSM-5, phosphorus-activated ZSM-5, ion-exchanged ZSM-5, MCM-22, and MCM-36, metal-exchanged zeolites, ITQs, SAPOs, ALPOs, and mixtures thereof. The slurry preferably comprises 5 to 60 wt % of one or more zeolite based on the final catalyst.

As will be discussed below, a second silica source may be added to the slurry at any point prior if the second silica source is acidic colloidal silica. If the second silica source is a polysilicic acid, it is made inline and added just after the addition of the zeolites and prior to the mixing of the next step. An exemplary polysilicic acid is a sodium stabilized or sodium free polysilicic acid made inline of the process by mixing appropriate amounts of sulfuric acid and water glass.

The above slurry is then passed through a high sheer mixer where it is destabilized by increasing the pH. The pH of the slurry is subsequently adjusted to a value above 3, more preferably above 3.5, even more preferably above 4. The pH of the slurry is preferably not higher than 7, because slurries with a higher pH can be difficult to handle. The pH can be adjusted by adding a base (e.g. NaOH or $NH_4OH$) to the slurry. The time period between the pH adjustment and shaping step d) preferably is 30 minutes or less, more preferably less than 5 minutes, and most preferably less than 3 minutes. At this step, the solids content of the slurry preferably is about 10 to about 45 wt %, more preferably about 15 to about 40 wt %, and most preferably about 25 to about 35 wt %.

The slurry is then shaped. Suitable shaping methods include spray-drying, pulse drying, pelletising, extrusion (optionally combined with kneading), beading, or any other conventional shaping method used in the catalyst and absorbent fields or combinations thereof. A preferred shaping method is spray-drying. If the catalyst is shaped by spray-drying, the inlet temperature of the spray-dryer preferably ranges from 300 to 600° C. and the outlet temperature preferably ranges from 105 to 200° C.

Silica Sources

A unique feature of the present invention is the use of at least two sources of silica within the catalyst particle. The total amount of silica added is greater than 1.0%. It is preferred that the total silica is greater than about 5.0% and it is most preferred that the total amount of silica is greater than about 10.0%. Further, it is preferred that ratio of the first silica source to the second silica source is from about 1:1 to about 1:10.

The first source of silica is typically a low sodium silica source and is added to the initial slurry. Examples of such silica sources include, but are not limited to potassium silicate, sodium silicate, lithium silicate, calcium silicate, magnesium silicate, barium silicate, strontium silicate, zinc silicate, phosphorus silicate, and barium silicate. Examples of suitable organic silicates are silicones (polyorganosiloxanes such as polymethylphenyl-siloxane and polydimethylsiloxane) and other compounds containing Si—O—C—O—Si structures, and precursors thereof such as methyl chlorosilane, dimethyl chlorosilane, trimethyl chlorosilane, and mixtures thereof. Preferred low sodium silica sources are sodium stabilized basic colloidal silicas. The slurry further comprises greater than 0 to about 15 wt % and more preferably greater than about 0.5 to about 10 wt % of silica from the low sodium silicon source based on the weight of the final catalyst and most preferred greater than about 1 wt % to 8 wt %.

The second silica source is typically a low sodium or sodium free acidic colloidal silica or polysilicic acid. Suitable silicon sources to be added as a second silica source include (poly)silicic acid, sodium silicate, sodium-free silicon sources, and organic silicon sources. One such source for the second silica is a sodium stabilized or sodium free polysilicic acid made inline of the process by mixing appropriate amounts of sulfuric acid and water glass. This second addition of silica is added in an amount of greater than about 0 to 30 wt %, preferably greater than about 1 wt % to about 25 wt % and most preferably about 5 to about 20% based on the weight of the final catalyst.

The choice of the second silica source can have an effect on when the material is added to the slurry discussed above. If acidic colloidal silica is used, then the silica may be added at any step prior to the pH adjustment step. However, if the second silica source is a sodium stabilized or sodium free polysilicic acid, the silica should be added after the zeolite addition just prior to the pH adjustment step. In addition, due to the sodium content of the polysilicic acid it may be necessary to wash the final catalyst to remove excess sodium. It may further be necessary or desirable to calcine the final catalyst.

The Resulting Catalyst

The catalyst so obtained has exceptionally good attrition resistance and accessibility. Therefore, the invention also relates to a catalyst obtainable by the process according to the invention. The catalyst is generally an FCC catalyst comprising about 5 to about 60% one or more zeolites, about 15 to about 35 wt % quasicrystalline boehmite, about 0 to about 25 wt % microcrystalline boehmite, greater than about 0 wt % to about 15 wt % silica from sodium stabilized basic colloidal silica, greater than about 0 wt % to about 30 wt % silica from acidic colloidal silica or polysilicic acid, and the balance clay.

These catalysts can be used as FCC catalysts or FCC additives in hydroprocessing catalysts, alkylation catalysts, reforming catalysts, gas-to-liquid conversion catalysts, coal conversion catalysts, hydrogen manufacturing catalysts, and automotive catalysts. The invention therefore also relates to the use of these catalyst obtainable by the process of the invention as catalyst or additive in fluid catalytic cracking, hydroprocessing, alkylation, reforming, gas-to-liquid conversion, coal conversion, and hydrogen manufacturing, and as automotive catalyst The process of the invention is particularly applicable to Fluid Catalytic Cracking (FCC). In the FCC process, the details of which are generally known, the catalyst, which is generally present as a fine particulate comprising over 90 wt % of the particles having diameters in the range of about 5 to about 300 microns. In the reactor portion, a hydrocarbon feedstock is gasified and directed upward through a reaction zone, such that the particulate catalyst is entrained and fluidized in the hydrocarbon feedstock stream. The hot catalyst, which is coming from the regenerator, reacts with the hydrocarbon feed which is vaporized and cracked by the catalyst. Typically temperatures in the reactor are 400-650 C and the pressure can be under reduced, atmospheric or superatmospheric pressure, usually about atmospheric to about 5 atmospheres. The catalytic process can be either fixed bed, moving bed, or fluidized bed, and the hydrocarbon flow may be either concurrent or countercurrent to the catalyst flow. The process of the invention is also suitable for TCC (Thermofor catalytic cracking) or DCC.

EXAMPLES

Prior to any lab testing the catalyst must be deactivated to simulate catalyst in a refinery unit, this is typically done with steam. These samples were deactivated either by cyclic deactivation with Ni/V which consists of cracking, stripping and regeneration steps in the presence of steam or with 100% steam at higher temperatures, which are industrially accepted deactivation methods for FCC catalysts. The deactivation step is known in the art, and is necessary to catalytic activity. In commercial FCC setting, deactivation occurs shortly after catalyst introduction, and does not need to be carried out as a separate step.

Accessibility Measurement. The accessibility of the catalysts prepared according to the Examples below was measured by adding 1 g of the catalyst to a stirred vessel containing 50 g vacuum gas oil. The solution was circulated between the vessel and a spectrophotometer, in which process the VGO-concentration was continuously measured. The accessibility of the catalysts to VGO was quantified by the Akzo Accessibility Index (AAI). The relative concentration of VGO in the solution was plotted against the square root of time. The AAI is defined as the initial slope of this graph:

$$AAI = -d(C_t/C_0)/d(t^{1/2})*100\%$$

In this equation, t is the time (in minutes) and $C_0$ and $C_t$ denote the concentrations of high-molecular weight compound in the solvent at the start of the experiment and at time t, respectively.

Attrition Resistance Measurement. The attrition resistance of the catalysts was measured by the standard Attrition Test. In this test the catalyst bed resides on an attrition plate with three nozzles. The attrition plate is situated within an attrition tube which is at ambient temperature. Air is forced to the nozzles and the resulting jets bring about upward transport of catalyst particles and generated fines. On top of the attrition tube is a separation chamber where the flow dissipates, and most particles larger than about 16 microns fall back into the attrition tube. Smaller particles are collected in a collection bag. This test is conducted after calcination of the catalyst samples at 600° C., and it is first run for 5 hours and the weight percentage of fines collected in the collection bag, based on an imaginary intake of 50 grams, is determined. This is the initial attrition. The test is then conducted for another 15 hours and the weight percentage of fines in this time period (5-20 hours) is determined. This is the inherent attrition. The Attrition Index (AI) is the extrapolated wt % fines after 25 hours. So, the more attrition resistant the catalyst is, the lower the AI value.

Example 1—Sodium Stabilized Polysilicic Acid. Five separate examples were made using the techniques described herein. Each separate example was compared to a base case of using a single silica source. The amount of each silica varied for each of the examples, as detailed below in the Table. Silica 1 is sodium stabilized basic colloidal silica and Silica 2 is a sodium stabilized poly silicic acid. After the spray dry, the catalysts of the present invention were subjected to a washing process to remove the sodium. It is evident from the physical properties (ABD and attrition) data shown below that all the catalysts of the present invention showed improved binding over either base case with a single silica. Also higher accessibility (AAI) and total surface area were noted on these catalysts. After deactivation, the MiPV % retention is above 20% higher for catalysts of the present invention in addition to around 5% higher surface area retentions than the prior art catalyst. In the following samples, the quasicrystalline boehmite level is same (20%) and the zeolite remains constant as well.

| Catalyst Description | Comp 1-1 | Ex. 1-1 | Ex. 1-2 | Ex. 1-3 | Ex. 1-4 | Ex. 1-5 | Comp 1-2 |
| --- | --- | --- | --- | --- | --- | --- | --- |
| Silica 1 | 1.5 | 15 | 10 | 10 | 5 | 5 | 0 |
| Silica 2 | 0 | 5 | 5 | 10 | 10 | 15 | 15 |
| ABD | 0.73 | 0.78 | 0.76 | 0.8 | 0.77 | 0.77 | 0.69 |
| Attrition | 2.17 | 0.94 | 1.22 | 0.42 | 0.25 | 0.48 | 1.47 |
| % improvement in Attrition | | 57% | 44% | 81% | 88% | 78% | |
| AAI | 9.1 | 14.8 | 14.8 | 9.3 | 9.9 | 7.8 | 3.7 |
| SA BET % Retention | 57% | 63% | 64% | 61% | 61% | 57% | 59% |
| MiPV BET % Retention | 50% | 68% | 68% | 68% | 70% | 72% | 64% |

Example 2—Sodium Free Polysilicic Acid. In this example, a sodium free polysilicic acid (Silica 3) replaces the sodium stabilized polysilicic acid (Silica 2) from the example above. The sodium free polysilicic acid was made just before spray drying the catalysts as the particle size grows with time and shows negative impact of both physicals and performance and added after the zeolites addition step. Since sodium free polysilicic acid is low sodium silica, it is not necessary to post-wash the catalyst after spray drying to remove the sodium. An example catalyst was made using the techniques described herein. Silica 1 is a sodium stabilized basic colloidal silica and Silica 3 is a sodium free poly silicic acid. The example was compared to a base case using a single silica source. Around 25% improvement in attrition and higher accessibility are noted on this catalyst compared to the base case. Cyclic deactivation of these catalyst showed that the surface area and MiPV % retentions are higher than base case catalyst which is consistent with the results with sodium stabilized polysilicic acid in the above examples. In the following examples, the quasicrystalline boehmite level is same (20%) for all examples and zeolite level is constant.

| Catalyst Description | Comp 2-1 | Ex. 2-1 |
|---|---|---|
| Silica-1 | 1.5 | 5 |
| Silica-3 | 0 | 15 |
| ABD | 0.72 | 0.72 |
| Attrition | 1.57 | 1.17 |
| % improvement in Attrition | | 25% |
| AAI | 9.2 | 11.9 |
| SA BET % Retention | 47% | 51% |
| MiPV BET % Retention | 47% | 65% |

Example 3—Acidic colloidal silicas. In order to avoid the post production washing process in the catalysts to remove the sodium when a sodium stabilized polysilicic acid is used, acidic colloidal silica sources were used. Below is an example of acidic colloidal silica (Silica 4) that replaces the sodium stabilized polysilicic acid (Silica 2) from the example above. Silica 4 is commercially available acid stabilized colloidal silica without any sodium content. It is reported that this silica has 1) a PSD of 20 nm, 2) a pH of 2.8 and
3) 30 wt % $SiO_2$. This silica fully replaced the sodium stabilized polysilicic acid (Silica 2) in the first set of examples and as shown below, it improved the catalyst ABD, surface area and attrition versus the base case. Upon cyclic deactivation, catalysts of the current invention with an acidic colloidal silica demonstrated better surface area and MiPV retentions than the base case. For each of the samples below, the quasicrystalline boehmite alumina level is same (20%) and the zeolite content remains constant.

| Catalyst Description | Comp 3-1 | Ex. 3-1 |
|---|---|---|
| Silica-1 | 1.5 | 5 |
| Silica-4 | | 15 |
| ABD | 0.63 | 0.8 |
| Attrition | 2.9 | 0.85 |
| % improvement in Attrition | | 71% |
| AAI | 12.3 | 11.2 |
| SA BET % Retention | 57% | 63% |
| MiPV BET % Retention | 51% | 63% |

Example 4—Steam deactivation: The benefits of these catalysts in physical properties and surface area and zeolite retention were further verified under different deactivation protocol (steam deactivation). An example catalyst with sodium stabilized polysilicic acid (Silica 2) as second silica source was made and compared with base case made with one silica source (Silica 1). Again the better attrition and ABD were noted on this catalyst as shown in the table below. After steam deactivation (788° C./20 h with 100% steam), the higher zeolite % retention was noted on the new catalyst compared to base case.

| Catalyst Description | Comp 4-1 | Ex. 4-1 |
|---|---|---|
| Silica-1 | 1.5 | 5 |
| Silica-2 | 0 | 15 |
| DBD | 0.70 | 0.83 |
| Attrition | 1.97 | 0.71 |
| % improvement in Attrition | | 64% |
| AAI | 11.2 | 10.8 |
| SA BET % Retention | 57% | 57% |
| MiPV BET % Retention | 45% | 68% |

Example 5—Varying Silica Content: Eleven separate examples were made using the techniques described herein. Each separate example was compared to a base case of using a single silica source. The amount of each silica varied for each of the examples, as detailed below in the Table. Silica 1 is sodium stabilized basic colloidal silica and Silica 4 is an acidic colloidal silica. It is evident from the physical properties (ABD and attrition) data shown below that the catalysts of the present invention showed similar or improved binding over base case with a single silica, with the exception of example 5-8. Higher accessibility (AAI) and total surface area were noted on these catalysts, in addition to increased MiPV retention. For the comparative sample below, the QCB content is 30 wt %, while the examples have a QCB content of 20 wt %. The total zeolite is the same throughout the cases.

| Catalyst Description | Comp 5-1 | Ex. 5-1 | Ex. 5-2 | Ex. 5-3 | Ex. 5-4 | Ex.5-5 | Ex. 5-6 | Ex. 5-7 | Ex. 5-8 | Ex. 5-9 | Ex. 5-10 | Ex. 5-11 |
|---|---|---|---|---|---|---|---|---|---|---|---|---|
| Silica 1 | 1.5 | 5 | 5 | 5 | 5 | 5 | 5 | 5 | 1.5 | 1.5 | 1.5 | 1.5 |
| Silica-4 | | 15 | 12 | 10 | 7 | 5 | 3 | 1 | 3.5 | 6.5 | 9.5 | 12.5 |
| ABD | 0.67 | 0.71 | 0.69 | 0.7 | 0.68 | 0.69 | 0.68 | 0.66 | 0.65 | 0.68 | 0.69 | 0.7 |
| Attrition | 2.365 | 1.36 | 1.425 | 1.43 | 1.915 | 1.595 | 1.9 | 2.375 | 2.765 | 2.11 | 1.77 | 1.44 |
| % improvement in Attrition | | 42% | 40% | 40% | 19% | 33% | 20% | 0% | −17% | 11% | 25% | 39% |
| AAI | 11.1 | 12.6 | 12.5 | 11.6 | 12.3 | 11.1 | 11.3 | 11.0 | 11.9 | 11.7 | 10.8 | 10.9 |
| SA BET % Retention | 56% | 64% | 61% | 61% | 62% | 59% | 62% | 61% | 60% | 62% | 62% | 61% |
| MiPV BET % Retention | 48% | 57% | 56% | 57% | 57% | 56% | 58% | 58% | 56% | 57% | 58% | 58% |

Example 6—Single Source Silica Study: One example was made using the techniques described herein. The example was compared to several base cases using varying amounts of a single source of silica. The amount of each silica varied for each of the examples, as detailed below in the Table. Silica 1 is sodium stabilized basic colloidal silica and Silica-4 is an acidic colloidal silica. The data indicates, in combination with the other examples throughout, that using one or more silica source provides similar or improved performance as to an equivalent amount of a single source of silica. Using more than one silica source, however, allows greater flexibility in formulations and provides benefits at low amounts of silica as well. For each of the samples below, the total alumina content is maintained throughout. The total zeolite level is maintained the same for all the catalysts. The examples below show that when a catalyst is made by the invention described herein, improved physicals are shown over the same total amount of a single source Silica 1 and similar physicals with respect to a single source of Silica 2. However, the use of at least 2 silica sources allows greater flexibility in product design and allows good physical characteristics with lower amounts of silica as shown throughout the examples.

| Catalyst Description | Comp 6-1 | Comp 6-2 | Comp 6-3 | Comp 6-4 | Comp 6-5 | Comp 6-6 | Comp 6-7 | Ex. 6-1 |
|---|---|---|---|---|---|---|---|---|
| Silica-1 | 1.5 | 5.0 | 10.0 | 20.0 | 0.0 | 0.0 | 0.0 | 5.0 |
| Silica-4 | 0.0 | 0.0 | 0.0 | 0.0 | 5.0 | 10.0 | 20.0 | 15.0 |
| ABD | 0.68 | 0.74 | 0.75 | 0.75 | 0.70 | 0.75 | 0.76 | 0.80 |
| Attrition | 3.67 | 1.84 | 1.03 | 0.99 | 1.98 | 1.30 | 0.85 | 0.93 |
| % improvement in Attrition |  | 50% | 72% | 73% | 46% | 65% | 77% | 75% |
| AAI | 12 | 11.9 | 11.7 | 11.6 | 11.4 | 10.5 | 11.4 | 10.6 |
| SA BET % Retention | 51% | 53% | 53% | 55% | 57% | 56% | 62% | 60% |
| MiPV BET % Retention | 40% | 44% | 49% | 53% | 45% | 46% | 55% | 53% |

The invention claimed is:

1. A process for manufacturing an FCC catalyst comprising:
   a. Adding, clay, boehmite and sodium stabilized basic colloidal silica to form a slurry;
   b. Digesting the slurry with a monoprotic acid to a pH of less than 4.0;
   c. Adding one or more zeolites to the slurry;
   d. Adding polysilicic acid made separately and added inline;
   e. Mixing the slurry and then destabilizing the slurry by raising the pH to above 4.0
   f. Shaping and collecting the resulting FCC Catalyst.

2. The process of claim 1 further comprising a calcination step and post washing step to remove excess sodium as necessary.

3. A process for manufacturing an FCC catalysts comprising:
   a. Adding, clay, boehmite, sodium stabilized basic colloidal silica to form a slurry;
   b. Digesting the slurry with a monoprotic acid to a pH of less than 4;
   c. Adding one or more zeolites to the slurry;
   d. Adding an acidic colloidal silica at any time during or after steps (a)-(c) but before step (e);
   e. Mixing the slurry and then destabilizing the slurry by raising the pH to above 4.0;
   f. Shaping and collecting the resulting FCC Catalyst.

* * * * *